(12) United States Patent
Nordstrom

(10) Patent No.: US 9,833,137 B1
(45) Date of Patent: Dec. 5, 2017

(54) METHOD AND APPARATUS FOR ADMINISTERING A LOW LUMINANCE VISUAL DYSFUNCTION TEST

(71) Applicant: Cheryl Nordstrom, Hinsdale, IL (US)

(72) Inventor: Cheryl Nordstrom, Hinsdale, IL (US)

(73) Assignee: Innova Systems, Inc., Burr Ridge, IL (US)

( * ) Notice: Subject to any disclaimer, the term of this patent is extended or adjusted under 35 U.S.C. 154(b) by 0 days.

(21) Appl. No.: 14/702,361

(22) Filed: May 1, 2015

Related U.S. Application Data

(60) Provisional application No. 61/987,986, filed on May 2, 2014.

(51) Int. Cl.
*A61B 3/00* (2006.01)
*A61B 3/02* (2006.01)
*A61B 3/028* (2006.01)
*A61B 3/032* (2006.01)
*A61B 3/06* (2006.01)

(52) U.S. Cl.
CPC ............... *A61B 3/022* (2013.01); *A61B 3/00* (2013.01); *A61B 3/0008* (2013.01); *A61B 3/0025* (2013.01); *A61B 3/0041* (2013.01); *A61B 3/028* (2013.01); *A61B 3/032* (2013.01); *A61B 3/0325* (2013.01); *A61B 3/06* (2013.01)

(58) Field of Classification Search
CPC ......... A61B 3/022; A61B 3/032; A61B 3/008; A61B 3/0033; A61B 3/0041; A61B 3/005; A61B 3/0091; A61B 3/02; A61B 3/028; A61B 3/0325; A61B 3/06; A61B 3/063
See application file for complete search history.

(56) References Cited

U.S. PATENT DOCUMENTS

| | | | | |
|---|---|---|---|---|
| 4,155,632 A | * | 5/1979 | Wolbarsht | A61B 3/032 351/232 |
| 8,419,184 B1 | * | 4/2013 | Butler | A61B 3/0285 351/205 |
| 2004/0027538 A1 | * | 2/2004 | Sinclair | A61B 3/028 351/224 |

(Continued)

OTHER PUBLICATIONS

Wu, Zhichao, et al., Low Luminance Visual Acuity and Microperimetry in Age-Related Macular Degeneration, Article n. Press Ophthalmology, 2014.

(Continued)

*Primary Examiner* — Jordan Schwartz
(74) *Attorney, Agent, or Firm* — Simpson & Simpson, PLLC

(57) ABSTRACT

A computerized method for administering a low luminance dysfunction test, comprising the steps of: (a) displaying a first character in a color at a first acuity level against a display having a luminance level; (b) receiving a first input signal from a patient via an input device, where the input signal is indicative of whether the patient recognizes the first character displayed in the first acuity level; (c) displaying a second character in the color at a second acuity level against the display having the luminance level; (d) receiving a second input signal from the patient via the input device, where the input signal is indicative of whether the patient recognizes the second character displayed at the second acuity level; and, (e) calculating a score based on the first and second input signals.

17 Claims, 2 Drawing Sheets

(56) References Cited

U.S. PATENT DOCUMENTS

| | | | | |
|---|---|---|---|---|
| 2004/0141152 | A1* | 7/2004 | Marino | A61B 3/032 351/222 |
| 2006/0238704 | A1* | 10/2006 | Donnerhacke | A61B 3/022 351/200 |
| 2008/0204662 | A1* | 8/2008 | Kanazawa | A61B 3/032 351/243 |
| 2011/0025977 | A1* | 2/2011 | Yoo | A61B 3/032 351/203 |
| 2012/0075586 | A1* | 3/2012 | Kirschen | A61B 3/032 351/239 |
| 2012/0120370 | A1* | 5/2012 | Lai | A61B 3/032 351/239 |
| 2013/0021579 | A1* | 1/2013 | Husain | A61B 3/032 351/246 |
| 2014/0285769 | A1* | 9/2014 | Palanker | G06Q 50/22 351/223 |

OTHER PUBLICATIONS

Sunness, Janet S., et al., Low Luminance Visual Dysfunction as a Predictor of Subsequent Visual Acuity Loss from Geographic Atrophy in Age-Related Macular Degeneration, Ophthalmology, vol. 115, No. 9, 2008, pp. 1480-1488.

Lad, Eleonora M, et al., Evaluation of Visual Function Impairments in Patients with Early and Intermediate Dry Age-Related Macular Degeneration, Duke University Medical Center, Durham, NC, United States, 2014.

Smith Kettlewell Institute, Low Luminance Visual Acuity (pp. 49-52), Feb. 14, 2013, Appendix C: Low Luminance Visual Acuity, Version 3.0.

Lad, Eleonora M., Evaluation of visual function impairments in patients with early and intermediate dry age-related macular degeneration, Duke University Medical Center, May 10, 2013, pp. 1-4.

Lad et al., Evaluation of Visual Function Impairments in Patients with Dry Age-Related Macular Degeneration, Investigative Ophthalmology & Visual Science Apr. 2014, vol. 55.

* cited by examiner

METHOD AND APPARATUS FOR ADMINISTERING A LOW LUMINANCE VISUAL DYSFUNCTION TEST

CROSS-REFERENCE TO RELATED APPLICATIONS

This patent claims the benefit under 35 U.S.C. §119(e) of U.S. Provisional Patent Application No. 61/987,986, filed May 2, 2014, which application is incorporated herein by reference in its entirety.

FIELD OF THE INVENTION

The invention broadly relates to eye tests for testing for low luminance visual dysfunction which may be used for the early detection, progress, treatment and monitoring of age-related macular degeneration (AMD) or other ocular diseases.

BACKGROUND OF THE INVENTION

Age-Related Macular Degeneration (AMD) is the leading cause of vision loss and blindness in the age group 65 and older. It is estimated that 6 million people in the United States alone are affected and with the aging Baby Boomer population, that figure is expected to grow at an explosive rate. AMD is a progressive disease with increased vision loss as the disease advances, particularly in the advanced stage. Drug companies are actively working to develop medications to slow or stop the advancement of dry AMD. In dry AMD, as opposed to wet AMD, cellular debris called drusen accumulates between the retina and the choroid, and the retina can become detached. There is a great need for a fast, repeatable, clinically-friendly test to serve as an end point in determining the efficacy of dry AMD treatment.

Most vision exams include a high-contrast visual acuity measurement. However, high-contrast visual acuity testing is ineffective in determining the presence or stage of dry AMD. Even advanced dry AMD patients may score at or near 20/20 visual acuity.

AMD patients often report difficulty seeing in dim lighting. "Even in the early stages of the disease when visual acuity is unaffected, these symptoms are present." Eleonora M. Lad, MD, PhD, *Evaluation of visual function impairments in patients with early and intermediate dry age related macular degeneration*. Research has shown that night vision loss may precede high-contrast visual acuity loss by two or more years in AMD patients and the difference in day and night vision may be able to not only identify AMD patients by stage of disease as well as serve to be a predictive factor in identifying patients in the highest risk category for VA vision loss.

"The mechanism behind an increased LLD in eyes with AMD is not clearly understood. It has been suggested that [Low-Luminance Visual Acuity] LLVA most likely reflects central cone-mediated function under reduced illumination." Wu, Zhichao, et al., *Low-Luminance Visual Acuity and Microperimetry in Age-Related Macular Degeneration*, Article in Press Ophthalmology, 2014. For example, it is suggested that "[i]t is foveal (central) cone function in particular that is the most critical for preservation of (Visual Acuity). A reduction in foveal cone function in dim illumination reduces (Visual Acuity) dramatically." Janet S. Sunness, MD; Gary S. Rubin, PhD; Aimee Broman, MS; Carol A. Applegate, COT; Neil M. Bressler, MD; Barbara S. Hawkins, PhD, *Low Luminance Visual Dysfunction as a Predictor of Subsequent Visual Acuity Loss from Geographic Atrophy in Age-Related Macular Degeneration*, Ophthalmology, Volume 115, Number 9, September 2008.

It has also been suggested that night vision loss is "associated with decreased sensitivity of the rod system responsible for vision in the dark. This is consistent with pathology results in eyes with AMD that showed that the rod photoreceptors degenerate earlier than cones in most patients with early AMD, despite good visual acuity." Id.

A patient's visual function differential from day and night can be measured by comparing high-contrast visual acuity with low luminance visual acuity, or low-luminance deficit (LLD). There is a great need for an automatic, fast, friendly, repeatable Low Luminance Deficit test for use in both clinical trials as well as clinic.

Another study suggests that low luminance cone function may be another predictor of VA loss in AMD. This study reported, "cone dark-adapted function is affected more than cone function under photopic conditions." Id. "Studies often compare dark-adapted rod function to light-adapted cone function and don't capture cone function in dim illumination." Id.

This theory is furthered by another study which reports, "eyes with drusen with reduced dark-adapted foveal sensitivity to a small red stimulus, advanced AMD was more likely to develop." Id. Even though Dark Adaptation, or adapting the eyes to total darkness, has also been shown to be highly diagnostic for early AMD, it is a lengthy process, making it impractical to use in clinic. There is a need for a device to rapidly measure cone function in dim illumination without requiring dark adaptation. Research shows that patients with early AMD have a substantial recovery period for rods and cones to regain function in darkness after being exposed to light, known as "bleaching", as compared to normal patient population free of eye disease.

Dark Adaptation is a lengthy process, taking 10-20 minutes to complete. The length of time required makes its use in a busy clinic impractical at best.

Currently, two recognized methods exist for measuring Low Luminance Deficit—the early treatment diabetic retinopathy study (ETDRS) light box used with neutral density filters and the Smith Kettlewell Institute Low Luminance Acuity Card (or SKILL Card). Both methods are manual, time consuming, and prone to scoring errors.

ETDRS Light Box

The ETDRS light box consists of a retro-illuminated light box with florescent tubes and a sleeve covering each tube, serving as a baffle to reduce illumination. The tubes must be burned in for four days and replaced every year. New models use light-emitting diode (LED) lighting, eliminating the need for baffling. ETDRS chart letters are displayed on the outside of the box.

The procedure to calculate LLD consists of three parts administered under normal lighting conditions: 1. Measuring the best corrected high contrast VA by testing the patient with the ETDRS chart at 4 or 1 meters (to size the optotypes accordingly), 2. Measuring the best corrected low luminance visual acuity (LLVA) by testing the patient at 4 or 1 meters with the ETDRS light box at either 4 or 1 meters (to size the optotypes according to patient acuity) with neutral density filters covering patient or trial lenses; 3. Calculating the VA score, LLVA score and LLD using an ETDRS worksheet.

Several limitations exist with the ETDRS light box due to the variation in bulb illumination as well as the manual nature of the test. Limitations of the ETDRS light box include: variance in acuity levels due to memorization of letter sequence; variance in acuity level due to luminance level variation as a result of bulb life; potential operator bias due to prompting; scoring error due to manual calculations and manual comparison of VA scores; lack of test friendliness due to different test distances and manual score calculations; lack of interface to electronic medical records; manual comparison of patient test scores over time; no darkness progression testing due to a single low luminance comparison.

SKILL Card

The SKILL Card consists of an ETDRS letter card with letters on a white background on one side and letters on a dark gray background, designed to simulate a reduced luminance environment, on the other side.

The SKILL card procedure consists of three parts at near distance under normal light conditions: 1. Measuring and calculating the near VA by reading from side one of the card; 2. Measuring and calculating the near LLVA from reading from side two of the card; 3. Calculating the VA, LLVA and LLD using an ETDRS worksheet.

Several limitations exist with the SKILL card due to the manual presentation of the test as well as room luminance variability. Limitations of the SKILL card include: variance in acuity levels due to memorization of letter sequence; variance in acuity level due to luminance level variation at card, potential operator bias due to prompting; scoring error due to manual calculation and manual comparison of VA scores; lack of test friendliness due to manual calculations; lack of interface to electronic medical records; manual comparison of patient test scores over time; no darkness progression testing due to single low luminance comparison.

Auto-Refractor

The Auto-Refractor uses wavefront technology to perform a daytime and nighttime refraction. It is a structural test that measures the shape of the eye to provide an initial refraction to be checked by a physician. Low Luminance Deficit reports are not available.

There is a great need for a rapid, standardized, automatic Low Luminance Deficit test that can: Score LLVA; Serve as a Classification System for Dry AMD; Serve as an End-point for AMD Clinical Trials; and Determine the Efficacy of AMD Treatment.

BRIEF SUMMARY OF THE INVENTION

The invention is a computerized method for administering a low luminance dysfunction test to a patient, comprising the steps of: (a) displaying a first character in a color at a first acuity level against a display having a luminance level, the display driven by the computer; (b) receiving a first input signal from the patient via an input device connected to the computer, where the input signal is indicative of whether the patient recognizes the first character displayed in the first acuity level; (c) displaying a second character in the color at a second acuity level against the display having the luminance level, the display driven by the computer; (d) receiving a second input signal from the patient via the input device connected to the computer, where the input signal is indicative of whether the patient recognizes the second character displayed at the second acuity level; and, (e) calculating a score based on the first and second input signals, the score related to acuity function in the patient's eye to the characters at the first and second acuity levels.

The present invention is designed to calculate and track low luminance dysfunction under low light and night conditions without the need to dark adapt. It calculates how much visual acuity loss a patient has in different environments. It may be a good indicator of dry AMD, making it a possible to show changes indicative to early, mid and late AMD, making it useful for both identifying the presence of dry AMD as well as determining the efficacy of treatment, including AMD drug treatment. U.S. patent application Ser. No. 14/251,286 (Nordstrom et al.) filed Apr. 11, 2014 is hereby incorporated by reference in its entirety.

The present invention includes: disease screening and management by physicians/technicians in the exam room in combination with other vision tests; disease screening and management by technicians in clinic screening rooms as a stand-alone test or combined with other vision tests; disease monitoring by patient at-home device with alerts or patient information sent to doctor.

The present invention includes a rapid functional self-test which quantifies Low Luminance Deficit and aids in predicting those patients most at risk for near-term visual acuity loss from AMD. For example, a particular increase in LLD can indicate early AMD. Early AMD patients report having difficulty with night vision even with normal acuity function. Identifying patients with Low Luminance Deficit allows the clinician to proactively target patients that may benefit most from proactive treatment.

The method and apparatus for testing for low luminance deficit:
  Provides rapid screening for Dry AMD;
  Aids in identifying patients most at risk for AMD-related VA loss;
  Compares patients results to AMD Stage Classification; and,
  Helps determine efficacy of treatment.

The test for low luminance deficit measures both high-contrast and low luminance visual acuity using black and/or colored letters. Several luminance level options are available for testing in lighting similar to low restaurant lighting and night driving. The standard LLVA value presentation is consistent with the 100 fold reduction of the neutral density filters and SKILL card, providing Standardized Scores comparable to these methods. Unlike conventional methods, automatic scoring makes the test quick, easy and reliable.

Reports are presented in graphical format and are easy to interpret. Comparison Reporting of patient results over time allow for better management of disease progression and treatment efficacy.

The present invention is self-calibrating, providing standardized results that may be compared across devices and clinics. With further clinical trials, reports may be able to show results compared to AMD Stage Classification.

The present invention is available in three embodiments: Exam Lane, Screening Room, and At-Home.

The Exam Lane embodiment, or exam room embodiment, comprises a wall-mounted device coupled with a general purpose computer specially programmed for testing to be used in conjunction with acuity and other quality of vision tests, consolidating multiple testing capabilities into a single device. An "in-lane" embodiment is used in the ophthalmic lane along with other vision tests. This unit comprises a general purpose computer specially programmed for testing, a wireless input device, and a photometer, network interface software, and electronic medical records (EMR) interface software. Tests are taken at a distance and the computer is mounted on the wall in front of the patient. The user interface comprises a response monitor, tablet or keypad (preferably a wireless, touch-screen tablet or monitor) for the technician to input patient responses. Patient data can be stored encrypted on the local device for comparison reporting. If several ophthalmic lanes exist in a single practice, patient data can be stored on a network and accessed for comparing patient reports taken from several ophthalmic lanes. The system comprises a computer (including but not limited to desktop, laptop, notebook, tablet, or all-in-one versions), photometer (for example, the SPYDER4™ photometer available from DATACOLOR of Lawrenceville, N.J.), and custom software.

The Screening Room embodiment comprises a portable device coupled with a general purpose computer specially programmed for testing that isolates self-testing from the exam lane, thereby speeding up patient throughput. It communicates with EMR so results may be reviewed in the exam lane with the patient. A screening room device used in a screening room or waiting room comprises automated tests for the patient to administer with little or no supervision. This unit comprises custom testing software, a touch-screen tablet, optionally a separate photometer, network interface software and EMR interface software. The user interface comprises a response pad on the touch-screen device for patient use. Patient data can be stored encrypted on the local device for comparison reporting. If several screening room devices are in use within a practice, patient data can be sent to the server for comparison reporting.

The At-Home embodiment helps physicians better monitor a patient between visits. This embodiment comprises exception-oriented alerts to notify a doctor and patient that immediate care is needed. This may allow physicians to schedule AMD patients based on need as opposed to calendar, allowing them to focus on those patients that most need their care. Test results are stored in the cloud and may be pulled down by the clinic server to update EMR. An at-home device used by the patient at home to monitor his/her condition in between appointments. This unit comprises automated tests for the patient to administer with no supervision. This unit comprises customer testing software, a touch-screen tablet or phone, optionally a separate photometer, notification to the preferred clinic likely via Cloud Technology. The user interface comprises a response pad on the touch-screen device for patient use. Patient data is stored encrypted on the local device for comparison reporting. Exception-oriented alerts are sent to the clinic for immediate care. Activation of the device is controlled on a periodic basis to accommodate leasing. Activation of the device is controlled by an activation code obtained via website login. Activation may be by the number of uses or time period to accommodate leasing.

The Low Luminance Cone Function embodiment of the present invention presents dark colored letters as opposed to black letters on a dark gray background. The description above applies also to this embodiment.

Benefits over current technology include:
Rapid staircase testing;
Randomized presentation, eliminating cheating;
Letter, Number and Symbol presentation, allowing use in all populations;
Automated/Interactive presentation sequence, eliminating technician bias;
Interactive patient response, eliminating technician bias;
Automatic calculation of Visual Acuity Letter Score and Low Luminance Acuity Loss, eliminating human bias in scoring;
Fully calibrated, yielding consistent luminance and results over time;
Inexpensive/Cost effective;
Readily available; and,
May be bundled with other Quality of Vision and Acuity tests for more thorough evaluation.

BRIEF DESCRIPTION OF THE SEVERAL VIEWS OF THE DRAWING

The nature and mode of operation of the present invention will now be more fully described in the following detailed description of the invention taken with the accompanying drawing figures, in which.

DETAILED DESCRIPTION OF THE INVENTION

Figure 1:
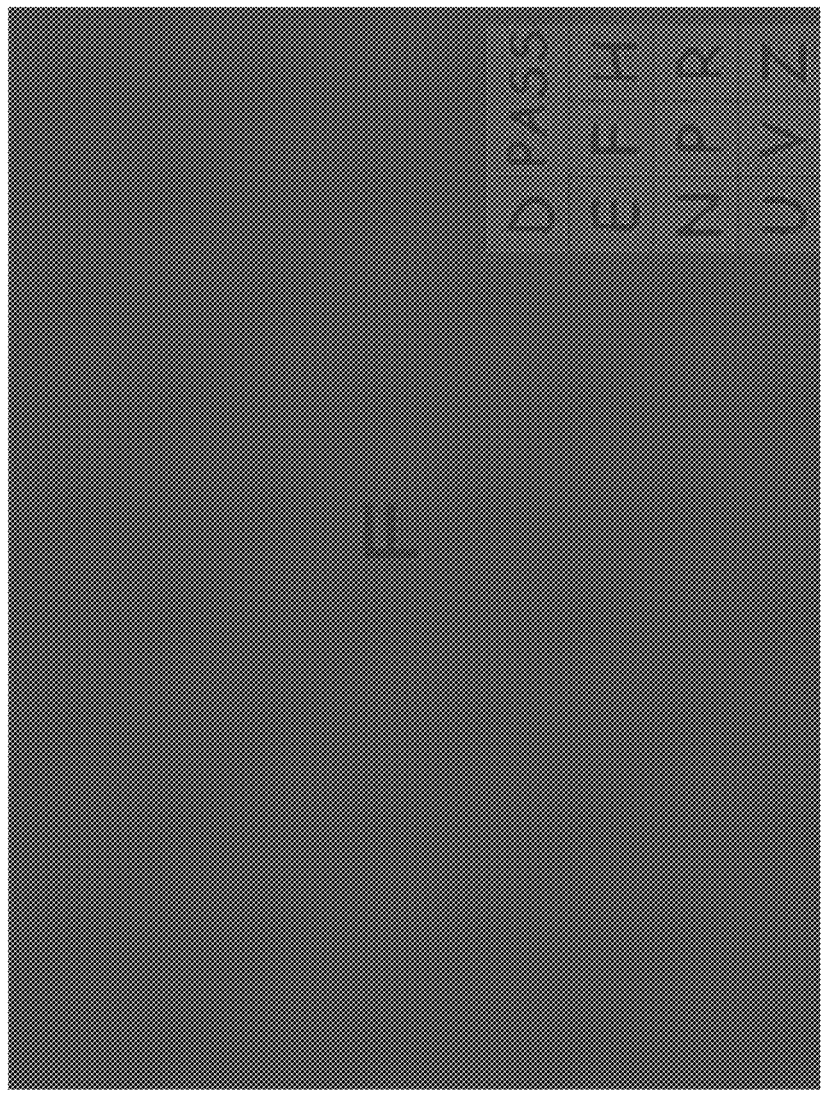
FIG. 1 is an example screen shot showing the invention with a response pad; and, FIG. 2 is an example screen shot showing the invention without a response pad.

It is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Technical specifications are as follows:
The display is calibrated for contrast levels.
A test includes at least two passes:
  Pass A: high contrast visual acuity (VA); and
  Pass B: one or more low luminance visual acuity with different low luminance values.
The passes are scored.
The scores are compared to determine the loss of acuity at a specific low luminance level.
Letters, numbers or symbols are presented on a low luminance background.
Acuity levels can be presented in Log MAR acuity increments to standardize results to ETDRS Charts.

| LogMAR Acuity Equivalence Chart | |
| --- | --- |
| 20/800 | 1.6 |
| 20/640 | 1.5 |
| 20/500 | 1.4 |
| 20/400 | 1.3 |
| 20/320 | 1.2 |
| 20/250 | 1.1 |
| 20/200 | 1.0 |
| 20/160 | 0.9 |
| 20/125 | 0.8 |
| 20/100 | 0.7 |
| 20/80 | 0.6 |
| 20/63 | 0.5 |
| 20/50 | 0.4 |
| 20/40 | 0.3 |
| 20/32 | 0.2 |
| 20/25 | 0.1 |
| 20/20 | 0.0 |

-continued

| LogMAR Acuity Equivalence Chart | |
|---|---|
| 20/16 | −0.1 |
| 20/12.5 | −0.2 |
| 20/10 | −0.3 |

The background luminance is presented at specific luminance in candela per meter squared, representing specific low light conditions, from dim indoor lighting (such as restaurant lighting) to moonlight. The first low luminance level for Pass B is 100 fold decrease in luminance over Pass A, simulating a neutral density filter worn over the patient's eye.

The specific luminance level may be selected by the administrator.

Test options include both near and distance.

Test options include monocular, single eye only, and binocular testing.

Letter size for acuity is sized for near testing at 18 inches, at distance testing based on lane length, or at standard 4 meters.

Each acuity level includes five letters for the full version and two letters for the staircase version, until the last acuity level presentation or a letter is missed, whichever comes first.

Target presentation times are of a fixed length, giving the patient a finite time to respond, ensure the test remains a rapid test.

Target presentation times may be set by the administrator based on the application-disease management versus super performance identification.

Beginning acuity level can be 1.0 Log MAR (or 20/200). In an example embodiment, the beginning acuity level can be 20/100.

Acuity levels decrease in 0.1 Log MAR steps (to ensure standardized results with existing clinical trials), with the test ending at 20/10 or a row in which four letters were identified incorrectly.

If twenty or fewer letters are identified correctly, the test continues upward in 0.1 Log MAR steps to 1.6 Log MAR or (20/800).

The staircase method reduces the acuity level by 0.2 Log MAR steps until a letter is missed.

Upon a miss, it increases the acuity level by 0.1 and continues to decrease in 0.1 Log units until the completion of the test.

Scoring is done for each eye, each pass is one point for each letter identified correctly, up to the acuity level 20/800 (even if the acuity levels higher than the ending acuity level were not presented). In the Staircase version, each acuity level presented represents five points if passed, even if only two letters were presented.

The acuity level for each eye, each pass is calculated on the point score.

Reporting calculates the Loss in Low Luminance Acuity by eye as the difference between Pass A and Pass B; Pass A and Pass C, etc.

Target Letter Presentation

In an example embodiment, the test for visual acuity presents randomized black ETDRS letters on a white background for VA testing and black ETDRS letters on a dark gray background. In an example embodiment, the Low Luminance Cone Function test presents randomized red, green or blue ETDRS letters on a dark gray background. The two tests function the same with the exception of the color of letters presented. It should be appreciated that Snellen letters could be presented as well.

Luminance Level

Two or more luminance levels may be selected to represent different low luminance conditions, i.e., low restaurant lighting and night driving. The luminance level is selected at the beginning of the test and compared to high-contrast visual acuity. One luminance level can be set 100 times lower in luminance than the high contrast VA test so results may be compared to existing clinical trials using conventional methods described above.

User Interface

Figure 2:
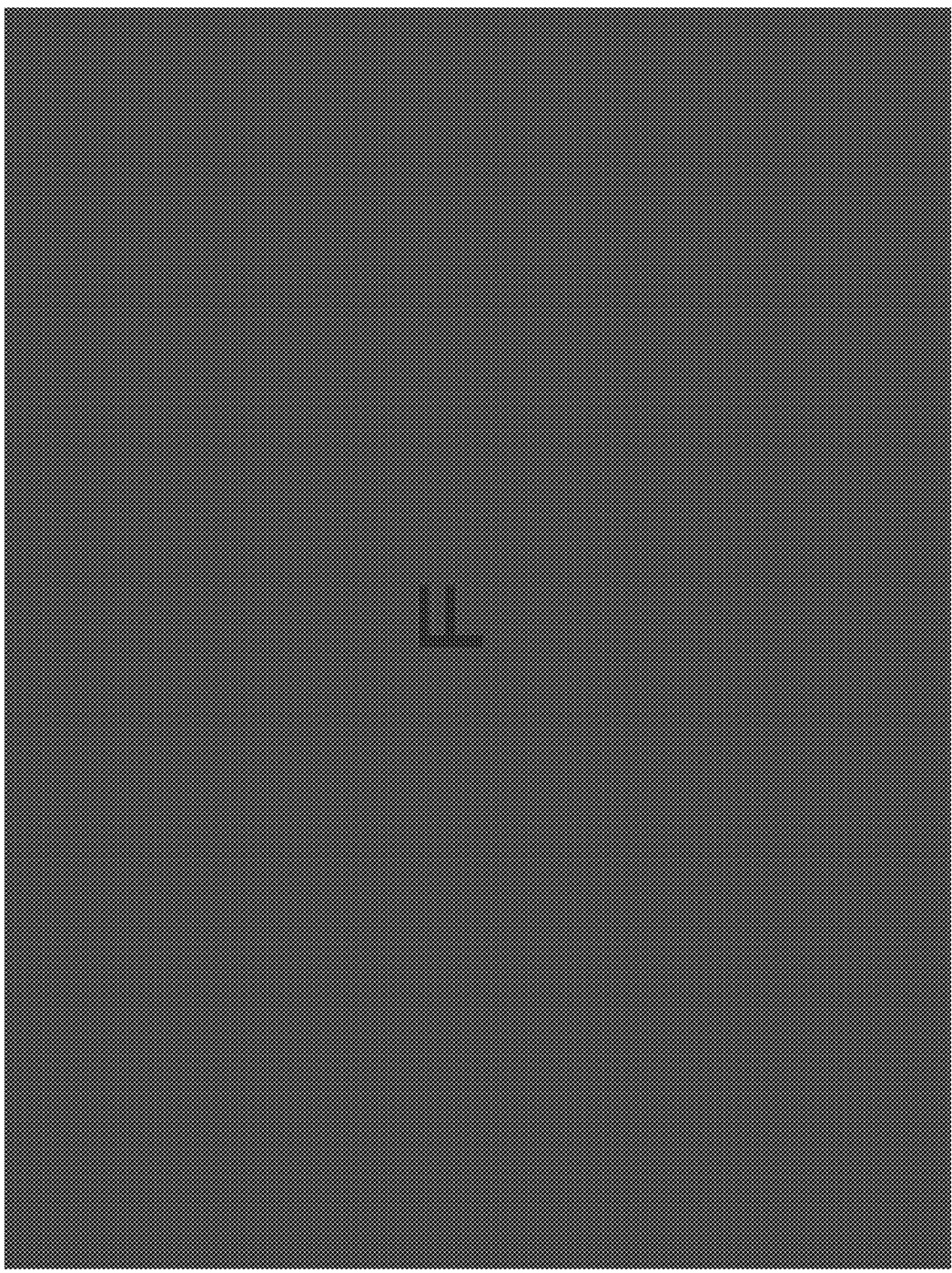

The patient responds via mouse click, touch screen or audibly to letters presented. The user interface comprises a response pad displayed on the display monitor, or a separate response device (monitor, tablet or keypad) for the technician to input patient responses. It should be appreciated that in an example embodiment, the response pad is displayed alongside the letters presented as shown in FIG. 1. Alternatively, as shown in FIG. 2, the response pad can be displayed within a device separate and distinct from the letters presented.

Additionally, it should be appreciated that the display pad can exhibit the possible responses against a backdrop having a greater contrast so that the patient can decipher the possible responses even if they cannot recognize the letter presented in low luminance. The response pad must be presented so the patient can see to respond without it interfering with the low-luminance test condition. The response pad may be a slightly lighter shade of gray or a colored background, such as red.

Patient information, including identification, name and date of birth is collected for exam and comparison reporting.

Calibration

The display is calibrated for color, luminance and contrast levels. Letters are sized for near testing at arms distance of 18 inches for touch screen monitors and for distance testing based on lane length.

Luminance Levels

The present invention comprises two passes: Pass A: high contrast visual acuity and Pass B: black letter low luminance visual acuity, with luminance level selected at the beginning of the test.

The Low Luminance Cone Function embodiment comprises two passes: Pass A: high contrast visual acuity and Pass B: colored letter low luminance visual acuity, with luminance level selected at the beginning of the test.

The background luminance is presented at specific luminance in candela per meter squared, representing specific low light conditions, from dim indoor lighting (such as restaurant lighting) to moonlight. In an example embodiment, the low luminance level of 0.5 $cd/m^2$ is selectable. Additionally, normal room lighting between approximately 100 and 150 c $d/m^2$ can be used.

The specific luminance level may be selected by the administrator at the beginning of the test.

In an example embodiment, the high contrast VA includes black lettering on a white background where the contrast >90% and the low luminance VA includes black lettering on a dark gray background constituting 10% of the reflectance of white.

Testing Options

Test options include both near distance and far distance. Test options include monocular, single eye only, and binocular testing. Test may be presented with letters, numbers or symbols. It should be appreciated that any character may suffice.

Staircase Methodology

Each acuity level presented comprises a total of five letters. Two letters are presented for each acuity level, until the last acuity level presentation or a letter is missed, whichever comes first. The last acuity level or any acuity level after an incorrect letter is identified comprises five letters. Beginning acuity level is 1.0 Log MAR (or 20/200), for example. If the patient responds correctly to two letters at a given acuity level, the acuity level decreases in 0.2 Log MAR units until a letter is missed or the last acuity level is presented. If the patient responds incorrectly to a letter at the initial acuity level, the acuity level increases in 0.1 Log MAR units until the patient correctly identifies all five letters on a given acuity level or the test reaches its highest acuity level of 1.6 Log MAR (or 20/800). If the patient responds incorrectly to a letter at an acuity level other than the initial acuity level, the acuity level increases by 0.1 Log MAR units and continues to decrease in 0.1 Log MAR units until the completion of the test.

Presentation Times

Target presentation times are of a fixed length, giving the patient a finite time to respond, ensuring the test remains a rapid test. Target presentation times may be set by the administrator based on the application, for example, disease management versus super performance identification.

Scoring

In an example embodiment, the total possible Raw Score for each eye is 100 points if patient correctly identifies all letters at the 20/10 level. Each acuity level passed without a miss is 5 points. Any partial acuity level is scored as one point for each letter correctly identified. Acuity levels which were skipped due to correctly identifying lower acuity levels receive 5 points per level. Low Luminance Deficit is the difference in raw score between the VA and LLVA. The raw score is presented along with the number of acuity levels differing between VA and LLVA with 5 points per level. Three points or more on a line rounds to the next acuity level.

Reporting

The Patient Exam Report shows for each eye: acuity lines presented, the number of letters presented and the number of correct responses for High Contrast VA and Low Luminance VA. For both VA and LLVA, the report shows the raw score, as well as the acuity level in Log MAR as described above.

It also shows in graphical format the VA and the LLVA in Log MAR units as well as the LLD in Log MAR units. The Patient Comparison Report shows per eye: the VA, LLVA and LLD in Log MAR raw score over time. Significant VA, LLVA, or LLD degradation is alerted. An example of a report is shown on the following page:

Innova Systems, Inc.
Night Vision Report
Patient Number:
Patient Name:
Date:

| | | Right Eye | | | | Left Eye | | | |
| --- | --- | --- | --- | --- | --- | --- | --- | --- | --- |
| | | VA | | LLVA | | VA | | LLVA | |
| Acuity | LogMAR | P | C | P | C | P | C | P | C |
| 20/100 | 0.7 | 2 | 2 | 2 | 2 | 2 | 2 | 2 | 2 |
| 20/80 | 0.6 | | | 2 | 2 | | | | |
| 20/63 | 0.5 | 2 | 2 | 5 | 1 | 2 | 2 | 2 | 2 |
| 20/40 | 0.3 | 2 | 2 | | | 2 | 2 | 2 | 2 |
| 20/32 | 0.2 | | | | | | | 5 | 5 |
| 20/25 | 0.1 | 2 | 2 | | | 2 | 2 | 2 | 0 |
| 20/20 | 0.0 | 5 | 4 | | | 5 | 4 | | |
| 20/10 | −.01 | 2 | 0 | | | 2 | 0 | | |
| Acuity Score | | | 84 | | 56 | | 84 | | 75 |

Right Eye Low Luminance Deficit: 28/ 6 Acuity Lines
Left Eye Low Luminance Deficit: 9/ 2 Acuity Lines Test Options:
Luminance Level: Night Driving—1 cd/meter2
Test Distance: Near—18 inches It should be appreciated that the present invention can be combined with a cone contrast test in a single device for the early detection, progress, treatment and monitoring of age-related macular degeneration (AMD) or other ocular diseases.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What is claimed is:

1. A computerized method for administering a low luminance dysfunction test to a patient, comprising the steps of:
   (a) displaying in high contrast a first character in a color at a first acuity level against a display producing a first luminance level, said display driven by said computer;
   (b) receiving a first input signal from said patient via an input device, where said input signal is indicative of whether said patient recognizes said first character displayed in said first acuity level;
   (c) displaying in high contrast a second character, being the same or different from the first character, the second character displayed in said color at a second acuity level, differing from the first acuity level, against said display producing said first luminance level, said display driven by said computer;
   (d) receiving a second input signal from said patient via said input device, where said input signal is indicative of whether said patient recognizes said second character displayed at said second acuity level;
   (e) calculating a first score based on said first and second input signals, said score related to acuity function in said patient's eye to said characters at said first and second acuity levels at said first luminance level;

(f) displaying a third character, being the same or different from the first and second characters, in said color at a third acuity level against the display producing a second luminance level, said second luminance level being lower than said first luminance level and selected prior to administering the test to replicate a specific low luminance real environmental condition, where low acuity function in the specific low luminance real environmental condition is used as an indicator of a visual dysfunction, said display driven by said computer;

(g) receiving a third input signal from said patient via an input device, where said third input signal is indicative of whether said patient recognizes said third character displayed at said third acuity level at said second luminance level;

(h) displaying a fourth character, being the same or different from the first, second, and third characters, in said color at a fourth acuity level, against said display producing said second luminance level, said display driven by said computer;

(i) receiving a fourth input signal from said patient via said input device, where said fourth input signal is indicative of whether said patient recognizes said fourth character displayed at said fourth acuity level at said second luminance level;

(j) calculating a second score related to acuity function in said patient's eye to said characters at said third and fourth acuity levels at said second luminance level; and, (k) calculating a degree of low luminance dysfunction by calculating a third score representing a difference between said first and second scores.

2. The method recited in claim 1, wherein said color is black.

3. The method recited in claim 1, wherein said color is red.

4. The method recited in claim 1, wherein said color is green.

5. The method recited in claim 1, wherein said color is blue.

6. The method recited in claim 1, wherein said second acuity level is lower than said first acuity level and said fourth acuity level is lower than said third acuity level.

7. The method recited in claim 1, further comprising the step of communicating said first, second, and third scores.

8. The method recited in claim 1, further comprising the step of storing said first, second, and third scores.

9. The method recited in claim 1, further comprising the step of printing said first, second, and third scores.

10. The method recited in claim 1, further comprising the step of displaying said first, second, and third scores.

11. The method recited in claim 1, further comprising the step of tracking said first, second, and third scores over time.

12. An apparatus for administering a low luminance dysfunction test to a patient, comprising:

(a) a general purpose computer specially programmed for displaying in high contrast a first character in a color at a first acuity level against a display producing a first luminance level, said display driven by said computer;

(b) means for receiving a first input signal from said patient via an input device, where said input signal is indicative of whether said patient recognizes said first character displayed in said first acuity level;

(c) means for displaying in high contrast a second character, being the same or different from the first character, the second character displayed in said color at a second acuity level, differing from the first acuity level, against said display producing said first luminance level, said display driven by said computer;

(d) means for receiving a second input signal from said patient via said input device, where said input signal is indicative of whether said patient recognizes said second character displayed at said second acuity level;

(e) means for calculating a first score based on said first and second input signals, said score related to acuity function in said patient's eye to said characters at said first and second acuity levels at said first luminance level;

(f) means for displaying a third character, being the same or different from the first and second characters, in said color at a third acuity level against the display producing a second luminance level, said second luminance level being lower than said first luminance level and selected prior to administering the test to replicate a specific low luminance real environmental condition, where low acuity function in the specific low luminance real environmental condition is used as an indicator of a visual dysfunction, said display driven by said computer;

(g) means for receiving a third input signal from said patient via an input device, where said third input signal is indicative of whether said patient recognizes said third character displayed at said third acuity level at said second luminance level;

(h) means for displaying a fourth character, being the same or different from the first, second, and third characters, in said color at a fourth acuity level, against said display producing said second luminance level, said display driven by said computer;

(i) means for receiving a fourth input signal from said patient via said input device, where said fourth input signal is indicative of whether said patient recognizes said fourth character displayed at said fourth acuity level at said second luminance level;

(j) means for calculating a second score related to acuity function in said patient's eye to said characters at said third and fourth acuity levels at said second luminance level; and, (k) means for calculating a degree of low luminance dysfunction by calculating a third score representing a difference between said first and second scores.

13. The apparatus recited in claim 12, wherein said color is black.

14. The apparatus recited in claim 12, wherein said color is red.

15. The apparatus recited in claim 12, wherein said color is green.

16. The apparatus recited in claim 12, wherein said color is blue.

17. The apparatus recited in claim 12, wherein said second acuity level is lower than said first acuity level and said fourth acuity level is lower than said third acuity level.

* * * * *